United States Patent
Nakayama

(10) Patent No.: US 12,378,512 B2
(45) Date of Patent: Aug. 5, 2025

(54) CULTURE APPARATUS FOR DRUG DISCOVERY RESEARCH

(71) Applicant: SAGA UNIVERSITY, Saga (JP)

(72) Inventor: Koichi Nakayama, Saga (JP)

(73) Assignee: SAGA UNIVERSITY, Saga (JP)

( * ) Notice: Subject to any disclaimer, the term of this patent is extended or adjusted under 35 U.S.C. 154(b) by 974 days.

(21) Appl. No.: 17/438,614

(22) PCT Filed: Mar. 13, 2020

(86) PCT No.: PCT/JP2020/012570
§ 371 (c)(1),
(2) Date: Sep. 13, 2021

(87) PCT Pub. No.: WO2020/189794
PCT Pub. Date: Sep. 24, 2020

(65) Prior Publication Data
US 2022/0213424 A1    Jul. 7, 2022

(30) Foreign Application Priority Data
Mar. 15, 2019    (JP) ................................ 2019-048228

(51) Int. Cl.
*C12M 1/12*    (2006.01)
*B33Y 80/00*    (2015.01)
(Continued)

(52) U.S. Cl.
CPC .............. *C12M 25/14* (2013.01); *B33Y 80/00* (2014.12); *C12N 5/0671* (2013.01);
(Continued)

(58) Field of Classification Search
CPC .............. C12N 2513/00; C12N 5/0671; G01N 33/5038; G01N 33/5014; B33Y 80/00; C12M 25/14
(Continued)

(56) References Cited

U.S. PATENT DOCUMENTS 8,198,086 B2 *   6/2012   Koga .................. C12N 5/0062
                                                            435/395
2011/0045500 A1   2/2011   Taniguchi et al.
(Continued)

FOREIGN PATENT DOCUMENTS

CN    101939416 A    1/2011
CN    108026498 A    5/2018
(Continued)

OTHER PUBLICATIONS

Arai et al., "Fabrication of scaffold-free tubular cardiac constructs using a Bio-3D printer," PLOS ONE (2018), vol. 13, No. 12, e0209162, pp. 2-18.
(Continued)

*Primary Examiner* — Michael L Hobbs
*Assistant Examiner* — Lenora A Abel
(74) *Attorney, Agent, or Firm* — Birch, Stewart, Kolasch & Birch, LLP

(57) ABSTRACT

A cell culture apparatus having a cell-holding container and a pinholder-shaped member comprising needle-shaped bodies arranged on a substrate, wherein a protruding part is formed in the center of the bottom surface of the cell-holding container, a recessed part is formed between the center and a side wall, and through-holes through which the needle-shaped bodies penetrate are established on the bottom surface of the recessed part; the needle-shaped bodies are arranged in correspondence with the positions of the through-holes; and the pinholder-shaped member is arranged, such that a tip-side portion of each of the needle-shaped bodies penetrates through the corresponding through-hole from the bottom surface side or upper surface side of the cell-holding container.

11 Claims, 10 Drawing Sheets

(51) Int. Cl.
  *C12N 5/071* (2010.01)
  *G01N 33/50* (2006.01)
(52) U.S. Cl.
  CPC ..... *G01N 33/5014* (2013.01); *G01N 33/5038* (2013.01); *C12N 2513/00* (2013.01)
(58) Field of Classification Search
  USPC ...................................................... 435/289.1
  See application file for complete search history.

(56) References Cited

U.S. PATENT DOCUMENTS

| | | |
|---|---|---|
| 2011/0200559 A1 | 8/2011 | Koga et al. |
| 2014/0120192 A1 | 5/2014 | Nakayama et al. |
| 2016/0348066 A1 | 12/2016 | Kuchiishi et al. |
| 2018/0201888 A1* | 7/2018 | Miwa ...................... C12M 1/22 |
| 2019/0359929 A1 | 11/2019 | Kishii et al. |

FOREIGN PATENT DOCUMENTS

| | | |
|---|---|---|
| EP | 2 725 091 A1 | 4/2014 |
| EP | 3 091 067 A1 | 11/2016 |
| JP | 4517125 B2 | 8/2010 |
| JP | 2015-213452 A | 12/2015 |
| JP | 2017-12109 A | 1/2017 |
| JP | 2017-79719 A | 5/2017 |
| JP | 2017-114069 A | 6/2017 |
| JP | 6334837 B1 | 5/2018 |
| WO | WO 2008/123614 A1 | 10/2008 |
| WO | WO 2018/207907 A1 | 11/2018 |

OTHER PUBLICATIONS

Office Application issued Aug. 2, 2022 in Japanese Patent Application No. 2021-507437.
Extended European Search Report for European Application No. 20773449.2, dated Nov. 14, 2022.
Chinese Office Action and Search Report for Chinese Application No. 202080020829.1, dated Sep. 18, 2023, with English translation.
Sheng et al., "Application of in vitro three-dimensional cell culture in pharma-toxicology study," Chin J Pharmacol Toxicol, vol. 21, No. 5, Oct. 2007, pp. 444-448, with an English abstract.
Zanoni et al., "3D tumor spheroid models for in vitro therapeutic screening: a systematic approach to enhance the biological relevance of data obtained," Scientific Reports, vol. 6, No. 19103, Jan. 11, 2016, 11 pages total.
International Search Report mailed May 26, 2020, in PCT/JP2020/012570.
Kizawa et al., "Scaffold-free 3D bio-printed human liver tissue stably maintains metabolic functions useful for drug discovery," Biochemistry and Biophysics Reports (2017), vol. 10, pp. 186-191.

* cited by examiner

Fig. 2
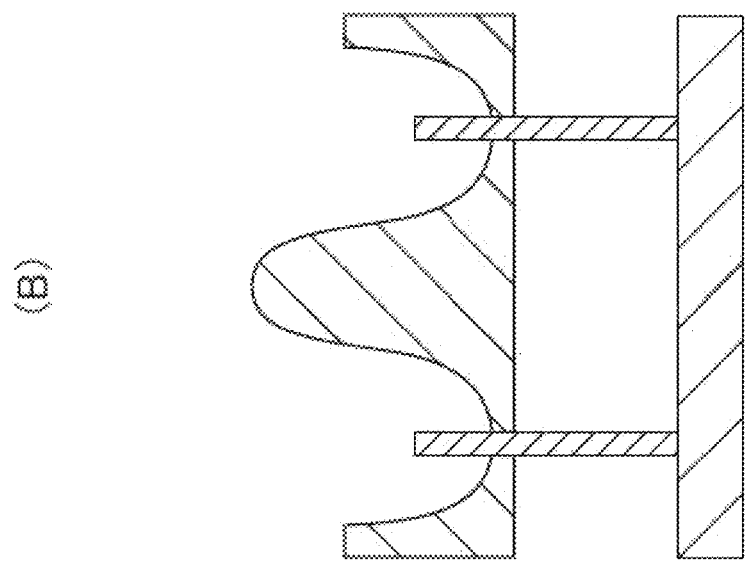
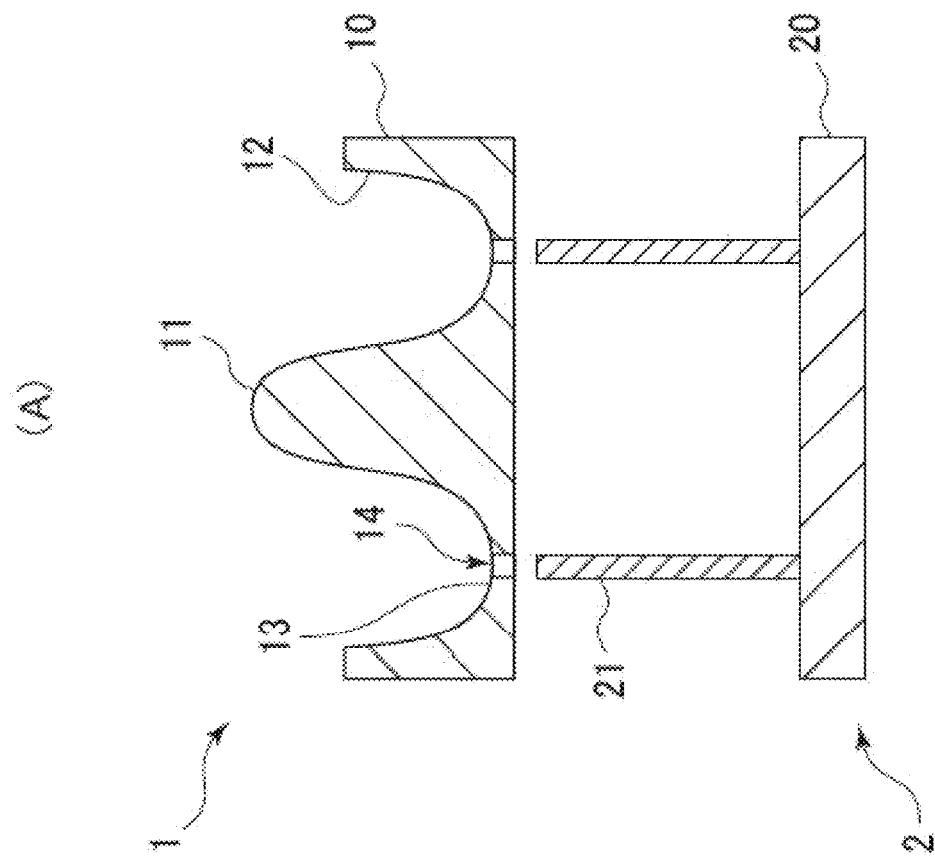

Fig. 5
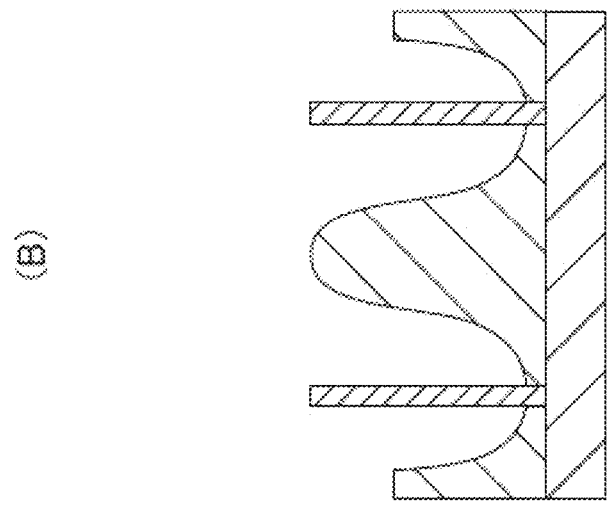
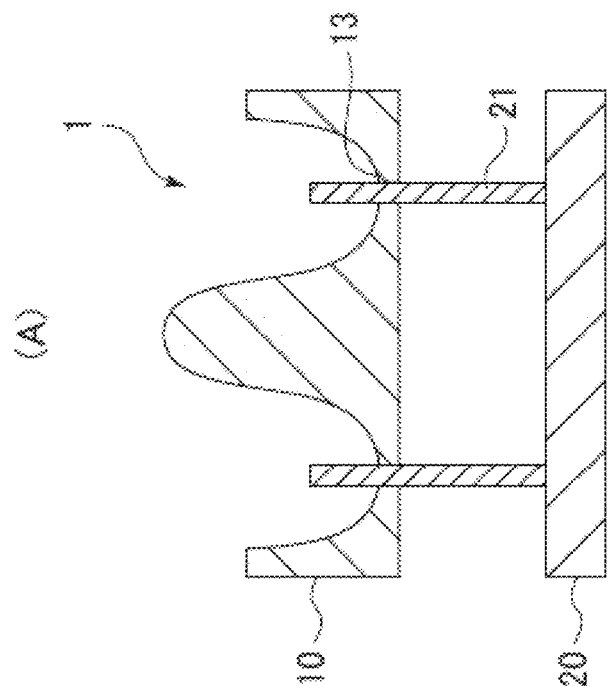

Fig. 6
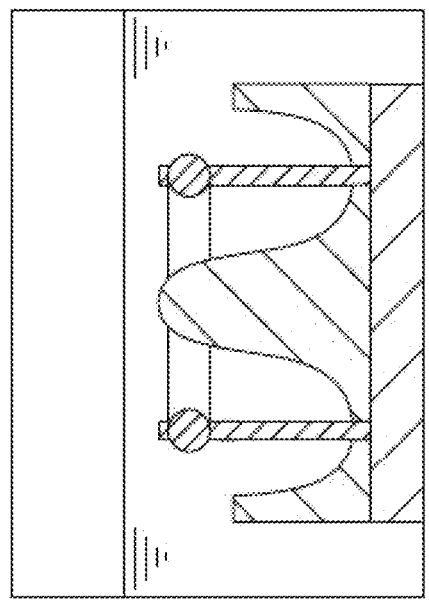
(A)
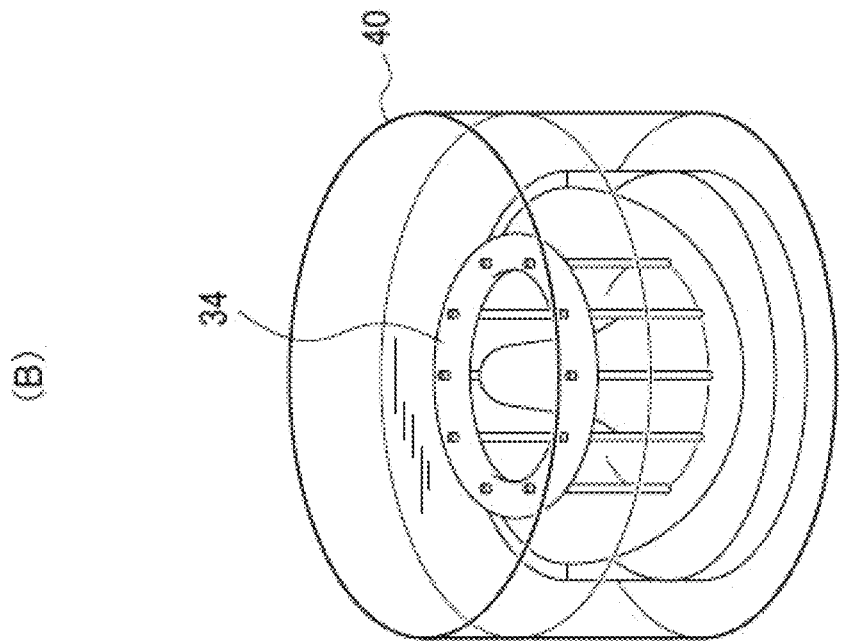
(B)

CULTURE APPARATUS FOR DRUG DISCOVERY RESEARCH

TECHNICAL FIELD

The present invention relates to an apparatus for culturing a three-dimensional cell structure, which is specialized in drug discovery research.

BACKGROUND ART

Conventionally, a technique of producing a three-dimensional cell structure by temporarily fixing a cellular aggregate (spheroid) in needles arranged in a pinholder shape has been known (Patent Literature 1). This technique is characterized in that a three-dimensional structure can be formed only with cells.

It has previously been known that spheroid culture provides higher cell activity than ordinary plate culture. In the three-dimensional cell structure form by the above-described technique, the cells are each transformed into three-dimensional forms, and thus, the cells have high metabolic activity. In addition, since the cells are directly contacted with a culture solution, the cells have high nutrient gas exchange efficiency.

In view of the foregoing, attempts have been made to use such a three-dimensional cell structure in a drug toxicity test and the like, and as a result, the human-specific hepatotoxicity of a drug, which could not have been detected by other human hepatocyte culture methods, could be detected (Non Patent Literature 1). Moreover, it is also likely that a three-dimensional structure constructed with myocardial cells can be utilized as a pulsation analysis tool.

In order to stick a spheroid into a pinholder, a special device (bio 3D printer) is required. However, since this device is expensive, it is difficult to acquire the device.

In drug discovery research, the number of spheroids, which is needed to be able to sufficiently analyze pharmacological activity, is 9. Thus, it is not necessary to use a bio 3D printer that treats a large number of spheroids (too high-spec device).

On the other hand, in order to carry out drug discovery, it is needed to treat a large amount of specimen at once. Hence, it has been desired to develop a screening system capable of performing a large-scale analysis with a small amount of cells.

PRIOR ART DOCUMENTS

Patent Literature

Patent Literature 1: Japanese Patent No. 4517125

Non Patent Literature

Non Patent Literature 1: Kizawa et, al., BBR 2017

SUMMARY OF INVENTION

Technical Problem

In order to carry out drug discovery, a screening system capable of performing a large-scale analysis with a small amount of cells has been desired. In addition, it has also been desired to develop a method for producing a simple and inexpensive cell structure that is for use in drug discovery tests.

Solution to Problem

The present inventor has conducted intensive studies directed towards achieving the aforementioned objects. As a result, the present inventor has successfully achieved the aforementioned objects by using a cell-holding container, in which the center on the bottom surface is formed as a protrusion and a recessed part is formed between the center and a side wall, thereby completing the present invention.

Specifically, the present invention is as follows.

(1) A cell culture apparatus having a cell-holding container and a pinholder-shaped member comprising needle-shaped bodies arranged on a substrate, wherein
a protruding part is formed in the center of the bottom surface of the cell-holding container, a recessed part is formed between the center and a side wall, and through-holes through which the needle-shaped bodies penetrate are established on the bottom surface of the recessed part,
the needle-shaped bodies are arranged in correspondence with the positions of the through-holes, and
the pinholder-shaped member is arranged, such that a tip-side portion of each of the needle-shaped bodies penetrates through the corresponding through-hole from the bottom surface side or upper surface side of the cell-holding container.

(2) A cell culture apparatus having a cell-holding container and a pinholder-shaped member comprising needle-shaped bodies arranged on a substrate, wherein
a protruding part is formed in the center of the bottom surface of the cell-holding container, and a recessed part is formed between the center and a side wall,
the needle-shaped bodies are arranged in correspondence with the positions of the bottom surface of the recessed part, and
the pinholder-shaped member is arranged, such that a tip of each of the needle-shaped bodies is directed from the upper surface side of the cell-holding container towards the bottom surface of the recessed part.

(3) The cell culture apparatus according to the above (1) or (2), wherein a plurality of the cell-holding containers and a plurality of the pinholder-shaped members are arranged in the form of an array.

(4) The cell culture apparatus according to any one of the above (1) to (3), wherein the cell-holding container is subjected to a cell non-adhesive coating treatment.

(5) A method for producing a cell structure, comprising pouring a cell suspension into a cell-holding container of the cell culture apparatus according to any one of the above (1) to (4), and agglutinating the cells so that the cells cover the needle-shaped bodies.

(6) The method according to the above (5), wherein the cells are hepatocytes or myocardial cells.

(7) A cell testing method, comprising contacting a test substance with a cell structure produced by the method according to the above (5) or (6), and testing the toxicity of the test substance to the cells or the metabolic activity of the cells in the cell structure.

(8) The method according to the above (7), wherein the cells are hepatocytes or myocardial cells.

(9) A cell testing device, including the cell culture apparatus according to any one of the above (1) to (4).

(10) The device according to the above (9), wherein the cells are hepatocytes or myocardial cells.

Effect of the Invention

According to the present invention, it has become possible to produce a simple and inexpensive cell structure, and thereby, it has become possible to carry out drug discovery tests such as cytotoxicity.

BRIEF DESCRIPTION OF DRAWINGS

FIG. 2 includes central cross-sectional views of the cell culture apparatus of the present invention.

FIG. 5 is a view showing an aspect in which a cell-holding container is slid in the longitudinal direction of needle-shaped bodies.

FIG. 6 is a view showing an aspect in which a cell structure is retained in a ring form at the tip portions of needle-shaped bodies.

DESCRIPTION OF EMBODIMENTS

The present invention provides a cell culture apparatus having a cell-holding container and a pinholder-shaped member comprising needle-shaped bodies arranged on a substrate, wherein
  a protruding part is formed in the center of the bottom surface of the cell-holding container, a recessed part is formed between the center and a side wall, and through-holes through which the needle-shaped bodies penetrate are established on the bottom surface of the recessed part,
  the needle-shaped bodies are arranged in correspondence with the positions of the through-holes, and
  the pinholder-shaped member is arranged, such that a tip-side portion of each of the needle-shaped bodies penetrates through the corresponding through-hole from the bottom surface side or upper surface side of the cell-holding container.

Figure 1:
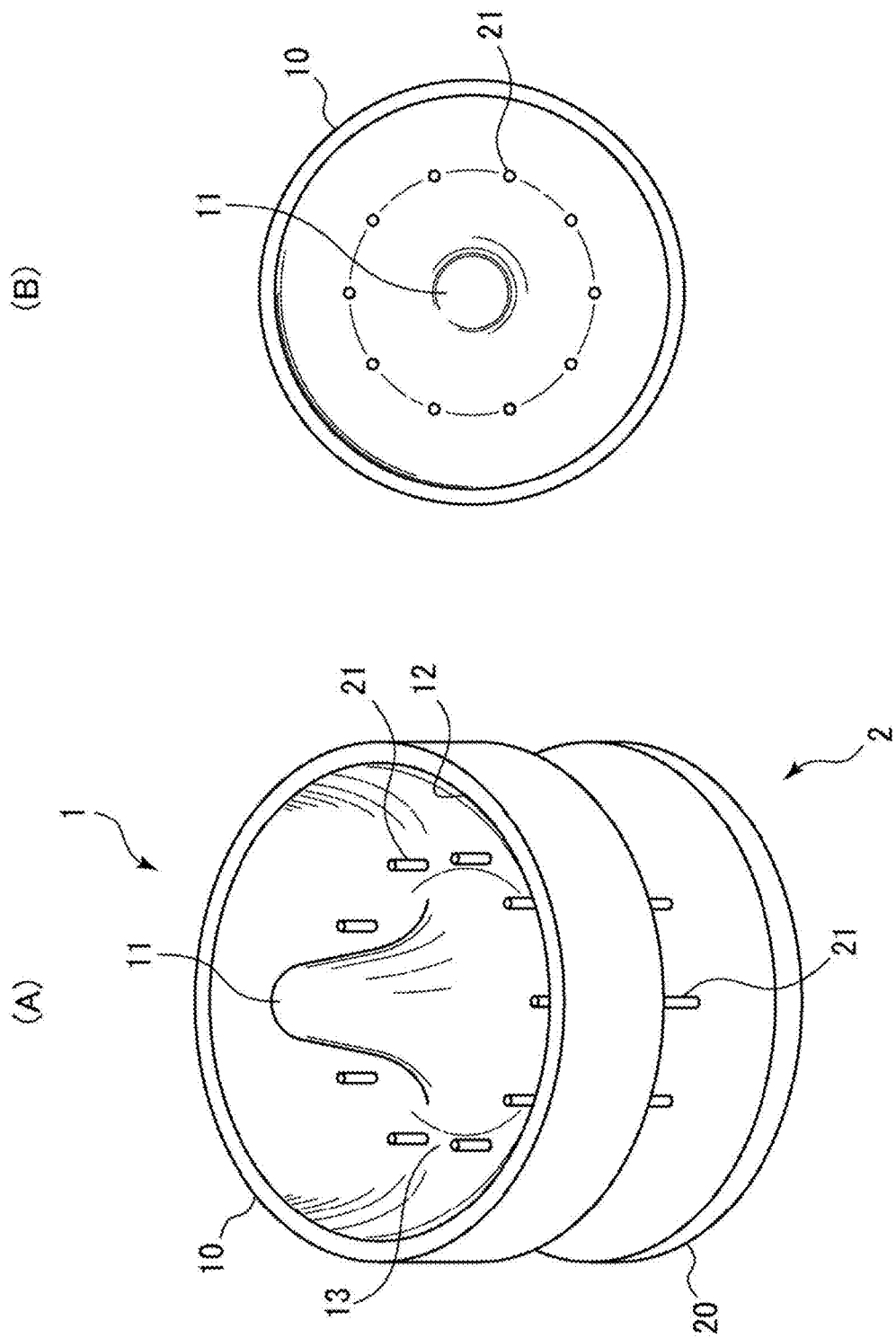
FIG. 1 is a view showing one aspect of the cell culture apparatus of the present invention.

An aspect of the cell culture apparatus of the present invention is shown in FIG. 1.

FIG. 1A is a perspective view of the cell culture apparatus of the present invention. A cell culture apparatus 1 comprises a cell-holding container 10, and a pinholder-shaped member 2 comprising needle-shaped bodies 21 arranged on a substrate 20.

A protruding part 11 is formed in the center of the bottom surface of the cell-holding container 10, and a recessed part 13 is formed between the center of the bottom surface of the cell-holding container 10 and a side wall 12. A shape, in which the center of the bottom surface becomes a protruding part and forms a recessed part between the center and the side wall, is similar to, what is called, a Mexican hat. Accordingly, in the present description, the cell-holding container 10 is also referred to as a "Mexican hat type culture vessel" or is simply referred to as a "hat type culture vessel."

FIG. 1B is a plan view obtained by seeing a cell culture apparatus 10 from above. In this aspect, ten needle-shaped bodies 21 are arranged on a substrate 20, and the needle-shaped bodies 21 are allowed to penetrate through through-holes 14 (as described later) of the cell-holding container 10 (the needle-shaped bodies 21 are arranged in correspondence with the positions of the through-holes 14).

FIG. 2 is a central cross-sectional view of a cell culture apparatus 1. In FIG. 2A, through-holes 14, through which needle-shaped bodies 21 on a pinholder-shaped member 2 penetrate, are established on the bottom surface 13 of a cell-holding container 10. Accordingly, the needle-shaped bodies 21 are arranged on a substrate 20, so that the needle-shaped bodies can be in correspondence with the positions of the through-holes 14 that are, for example, in the normal directions of the substrate 20. FIG. 2B shows an aspect, in which parts of needle-shaped bodies 21 on a pinholder-shaped member 2 are allowed to penetrate through the corresponding through-holes 14 from the bottom surface portions of a cell-holding container 10.

In the present invention, the recessed part 13 of the cell-holding container 10 forms a cell-holding part that holds cells, and when a cell suspension is poured into the recessed part 13, the cells simultaneously aggregate and form a spheroid, while covering a needle-shaped body.

Figure 3:
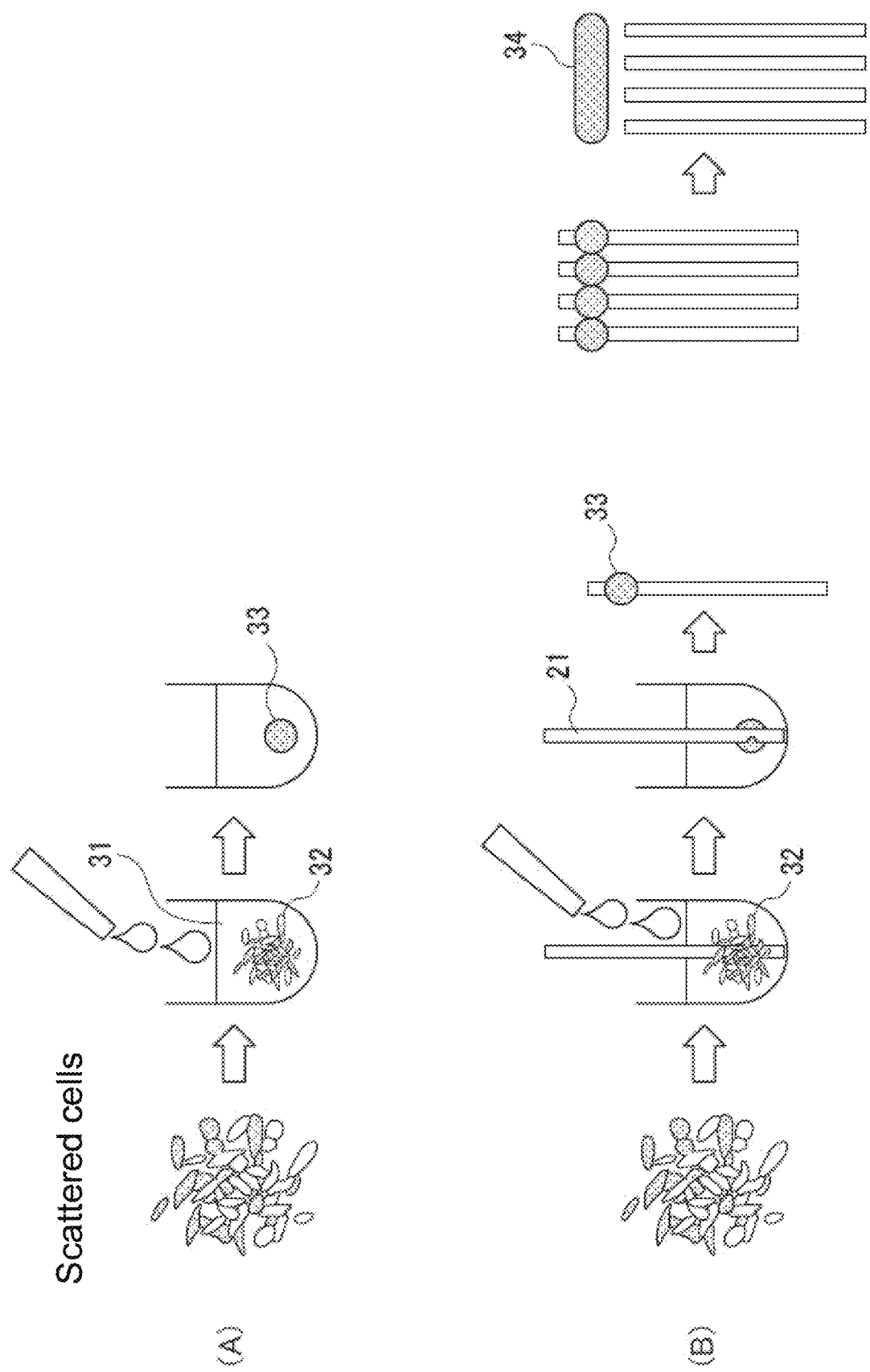
FIG. 3 is a view showing an aspect in which cells form spheroids, while covering needle-shaped bodies.

FIG. 3 is a schematic view showing an aspect in which cells form a spheroid, while covering a needle-shaped body.

FIG. 3A is a view showing an aspect of the formation of a spheroid in the absence of a needle-shaped body 21, and scattered cells 32 in a cell suspension 31 simultaneously aggregate and form a spheroid 33. In the present invention, as shown in FIG. 3B, by using a needle-shaped body 21, cells 32 form a spheroid 33, while covering a needle-shaped body 21. Since a plurality of the needle-shaped bodies 21 are arranged, for example, with equal intervals, the formed spheroids 33 are fused with one another, thereby producing a cell structure 34.

Herein, the type of the cells used in the present invention is not particularly limited, and any given cells that form a spheroid can be used. Examples of the cells that form a spheroid may include undifferentiated cells such as stem cells (ES cells, cord blood-derived cells, undifferentiated mesenchymal stem cells, adult mesenchymal stem cells, etc.), and the differentiated cells thereof. Examples of tissues, from which the cells used herein are derived, may include articular cartilage, bone, adipose tissues, ligaments, tendons, teeth, auricle, nose, liver, pancreas, blood vessels, nerve, and heart. Among these, hepatocytes, myocardial cells, and the like are preferable. In addition, the spheroid does not always need to be formed as an aggregate of a single type of cell. The spheroid may also be formed from multiple types of cells (for example, a mixture of hepatocytes and vascular endothelial cells), as long as the cells are able to form the spheroid.

Moreover, a culture period required to form a spheroid and a cell structure is different depending on the size of the cell culture apparatus 1. The culture period is approximately 2 days to 4 days under common culture conditions (for example, at 37° C., under 5% $CO_2$ atmosphere).

With regard to the material of the needle-shaped body 21, the needle-shaped body made of stainless steel, polypropylene, nylon, etc. can be used. However, the material of the needle-shaped body 21 is not limited thereto.

Moreover, the cell-holding container 10 has been preferably subjected to cell non-adhesive coating with fluorine, etc. (for example, a cell-holding container made of polydimethylsiloxane). However, a cell-holding container that has been subjected to fluorine processing or polyhydroxyethyl methacrylate polymer processing can also be used, and further, a cell-holding container made of an acrylic resin, an ABS resin, a polyester resin, a polycarbonate resin, polypropylene, polyethylene, polyacetal, polyether ether ketone, nylon, etc. can also be used.

Figure 4:
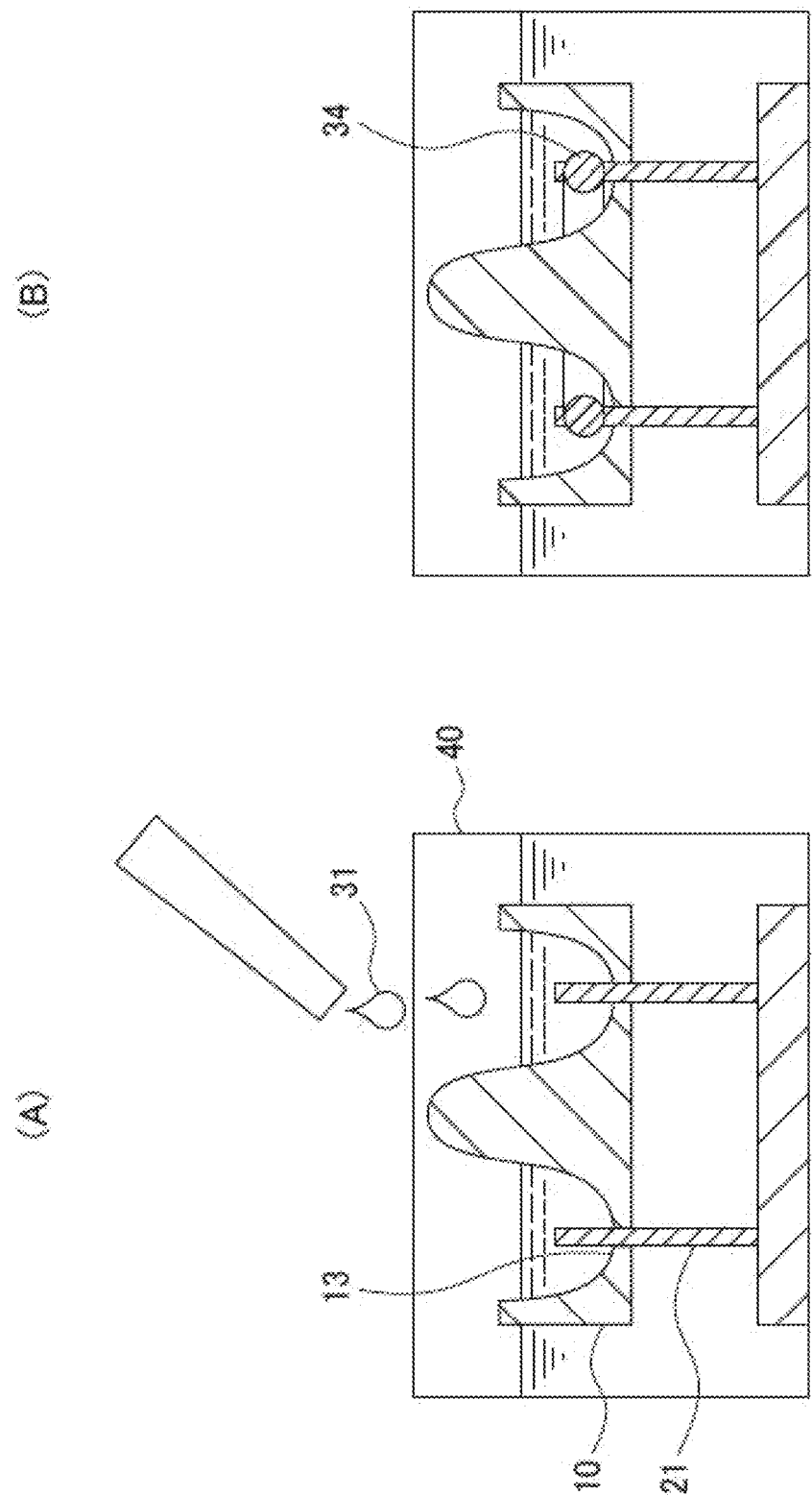
FIG. 4 is a view showing an aspect of producing a cell structure using the cell culture apparatus of the present invention.

FIG. 4 shows an aspect in which a cell structure 34 is produced using the cell culture apparatus 1 of the present invention, based on the mechanism of forming a cell structure 34, as shown in FIG. 3B.

First, a vessel 40 larger than the cell culture apparatus 1 of the present invention is filled with a culture solution, and the cell culture apparatus 1 is then placed in the vessel. The culture apparatus 1 has an aspect in which tip-side portions of needle-shaped bodies 21 on a pinholder-shaped member 2 penetrate through through-holes 14 of a cell-holding container 10. When a cell suspension 31 is poured into a recessed part 13 of the cell-holding container 10, the cells form spheroids, while covering the needle-shaped bodies 21, and at the same time, the spheroids are fused with one another to form a cell structure 34. In FIG. 1 or FIG. 4, the periphery of the cell-holding container 10 has a circular shape, and the recessed part 13 circularly surrounds the circumference of a protruding part 11 in the center of the bottom surface. Thus, the produced cell structure has a ring shape.

In the present invention, the shape of the periphery of the cell-holding container 10 is not limited to a circular shape, but it can be a polygon such as a rectangle, a pentagon, a hexagon or an octagon. Moreover, then number of the needle-shaped bodies 21 (i.e., the number of through-holes 14) is not limited, either, and it can be, for example, 2 to 20. When the cell-holding container 10 has a circular shape, the diameter thereof or the diameter of the recessed part 13 is not particularly limited, either, and it can be, for example, 0.6 mm to 30.0 mm.

FIG. 5 shows an aspect in which a cell-holding container 10 is slided in the longitudinal direction of needle-shaped bodies 21 in the cell culture apparatus 1 of the present invention.

When the cells are cultured, the cell-holding container 10 is arranged, so that the tip-side portions of the needle-shaped bodies 21 slightly protrude from through-holes 14, as shown in FIG. 5A. After construction of a cell structure 34, the cell-holding container 10 is slided downwards (on the side of a substrate 20) (FIG. 5B). Thereby, the cell structure 34 is retained in a ring form at the tip portions of the needle-shaped bodies 21 (FIG. 6). Hence, by sliding the cell-holding container 10 downwards, the area of the cell structure 34 established on the cell-holding container 10 is reduced, so that an analysis can be promptly carried out on the cell structure 34. For example, a test substance is placed into the cell-holding container 10 and/or the culture vessel 40, in the form of the cell structure 34 shown in FIG. 6, and thereafter, the activity or movement of the cell structure 34, the toxicity of the test substance to the cell structure 34, etc. can be examined.

Figure 7:
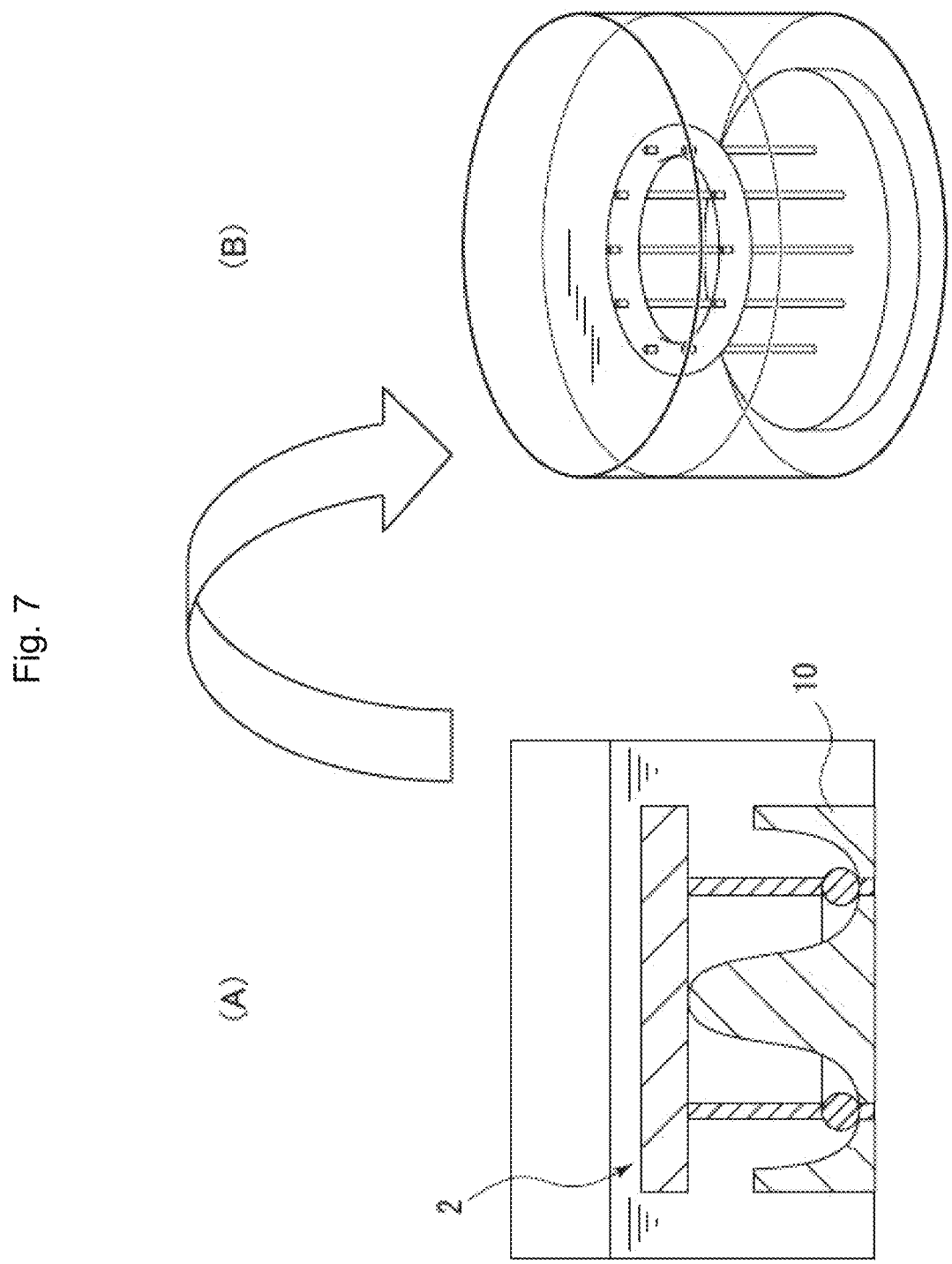
FIG. 7 is a view showing an aspect in which the tips of needle-shaped bodies on a pinholder-shaped member are arranged from the upper surface of a cell-holding container towards a recessed part.

FIGS. 1 and 2, etc. show an aspect in which the needle-shaped bodies 21 on the pinholder-shaped member 2 are allowed to penetrate from the bottom surface side of the cell-holding container 10 into the recessed part 13. On the other hand, FIG. 7 shows an aspect in which the tips of needle-shaped bodies 21 on a pinholder-shaped member 2 are arranged from the upper surface of a cell-holding container 10 towards a recessed part 13. In this case, through-holes 14 do not need to be established, and the establishment of the through-holes 14 is arbitrary. In order to fix the needle-shaped bodies 21, an aspect in which holes are established in the recessed part 13 of the cell-holding container 10 to such an extent that the holes do not penetrate (not shown in the figure) and the needle-shaped bodies 21 are inserted into the holes, may also be applied. As shown in FIG. 7A, the pinholder-shaped member 2 is arranged in the direction opposite to the aspect shown in FIG. 1, and a cell suspension is then poured therein, followed by the formation of spheroids and the formation of the cell structure 34. Thereafter, the direction of the pinholder-shaped member 2 is returned to the original direction (i.e, to face upwards), so as to achieve an aspect, in which the cell structures 34 are retained at the tips of the needle-shaped bodies 21. Besides, in this case, the substrate 20 can be removed.

Figure 8:
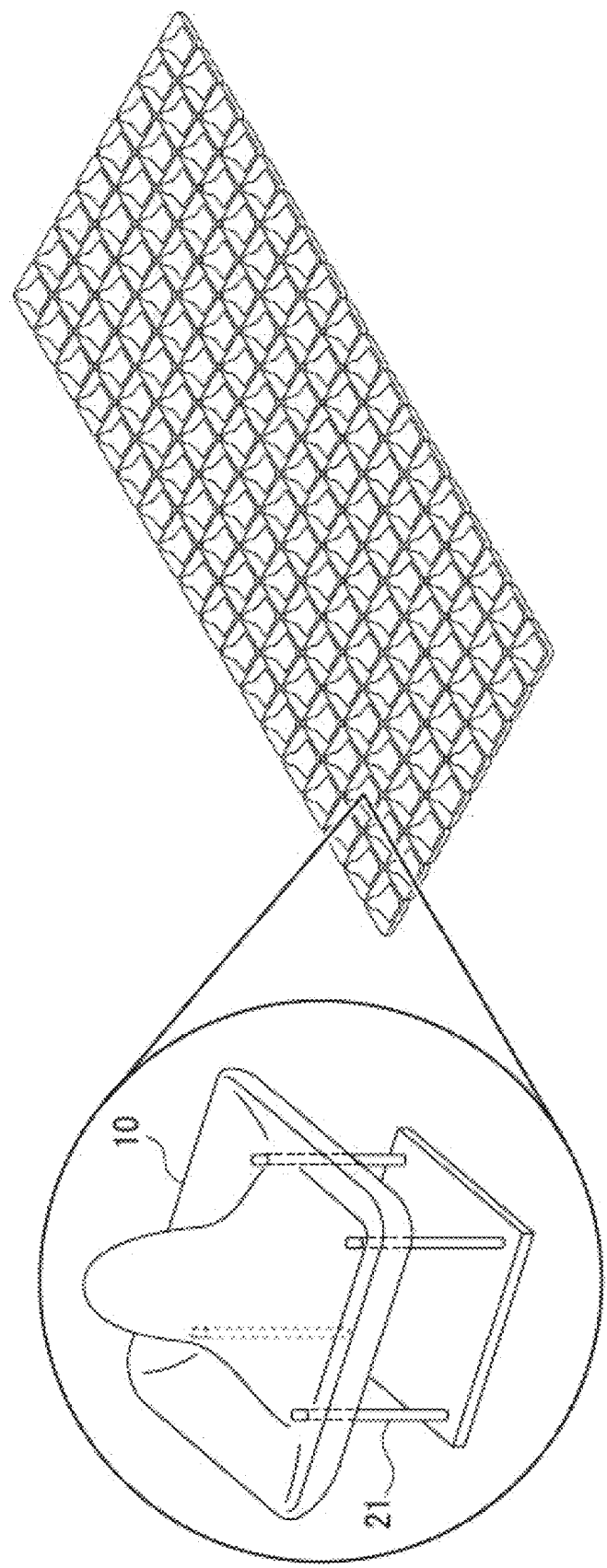
FIG. 8 is a view showing an aspect in which a plurality of the cell culture apparatuses of the present invention are arranged in the form of an array.

FIG. 8 is a view showing an aspect in which a plurality of the cell culture apparatuses 1 of the present invention are arranged in the form of an array.

In FIG. 8, the shape of a cell-holding container 10 is a square, and needle-shaped bodies 21 penetrate into 4 positions (4 corners) of a recessed part. Thus, by arranging the plurality of the cell culture apparatuses 1 of the present invention in the form of an array, a large number of cell structures 34 can be produced, and various types of tests can be carried out at once. Besides, with regard to the arrangement of the array, the array can be integrally molded.

Figure 9:
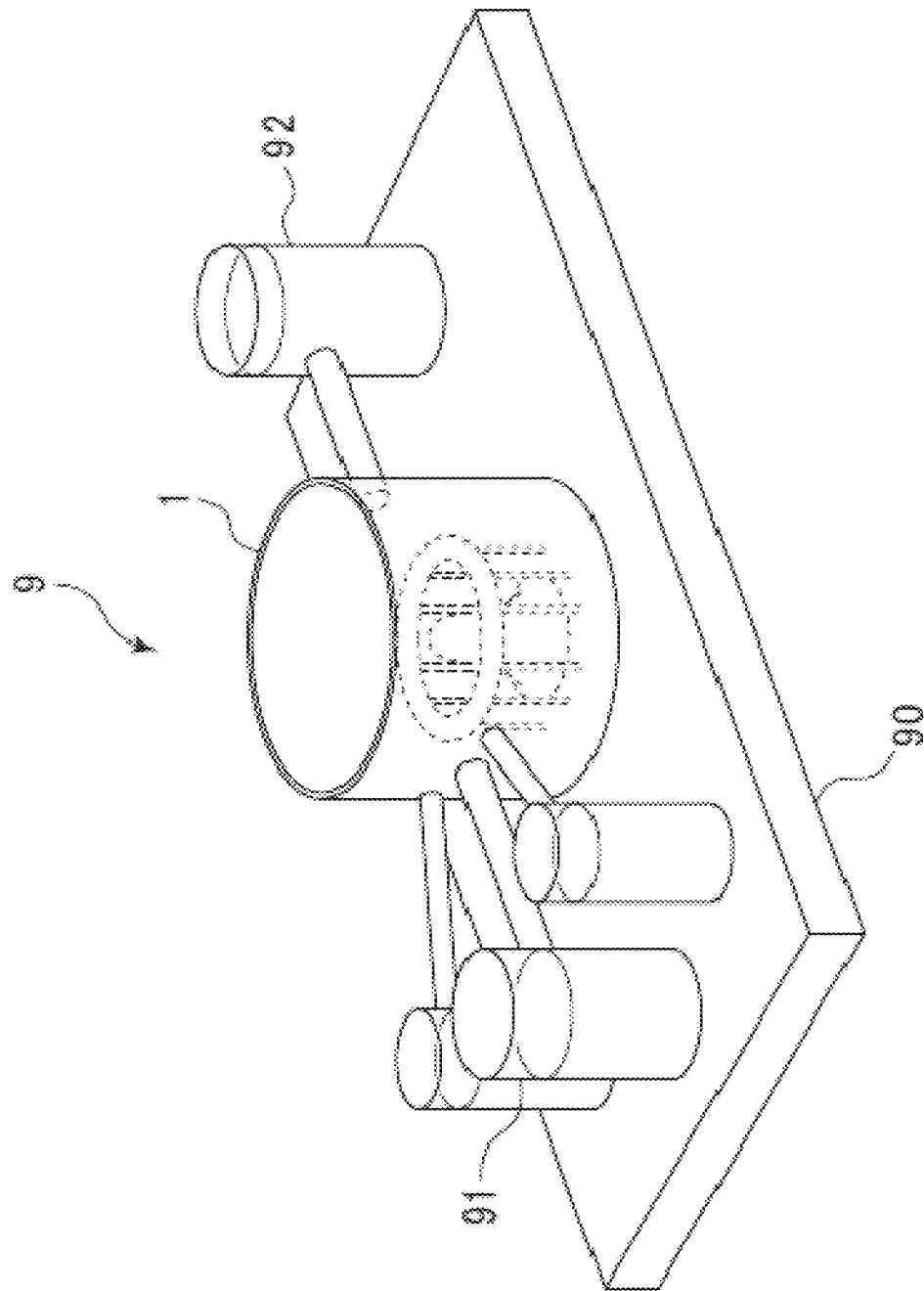
FIG. 9 is a view showing a cell testing device including the cell culture apparatus of the present invention.

FIG. 9 shows a view showing a cell testing device 9 including the cell culture apparatus 1 of the present invention. In the cell testing device 9, a cell culture apparatus 1 is established on a substrate 90, and a cell culture solution-supplying part 91 and a test substance-supplying part 92 are also established on the substrate 90. In the cell testing device 9, an electrode can be connected with needle-shaped bodies 21 (not shown in the figure).

Thereby, the metabolic activity of the cell structure, the pulsation of myocardial cells, or the like can be three-dimensionally examined.

Therefore, the present invention provides a cell testing method, which is characterized in that it comprises allowing a test substance to come into contact with a cell structure, and then testing the toxicity of the test substance to the cells or the metabolic activity of the cells.

Examples of the test substance may include naturally or artificially synthesized, various types of peptides, proteins (including enzymes and antibodies), nucleic acids (polynucleotides (DNA and RNA), oligonucleotides (siRNA, etc.), peptide nucleic acids (PNA), etc.), low molecular weight compounds, and polymeric organic compounds.

Moreover, the term "contact" means that a test substance is allowed to come into contact with the cell structure of the present invention. Examples of such contact may include: pouring a test substance into a culture vessel including a cell structure; and culturing a cell structure in a medium comprising a test substance.

EXAMPLES

Hereinafter, the present invention will be more specifically described in the following example. However, the following example is not intended to limit the scope of the present invention.

Example 1

Method

Figure 10:
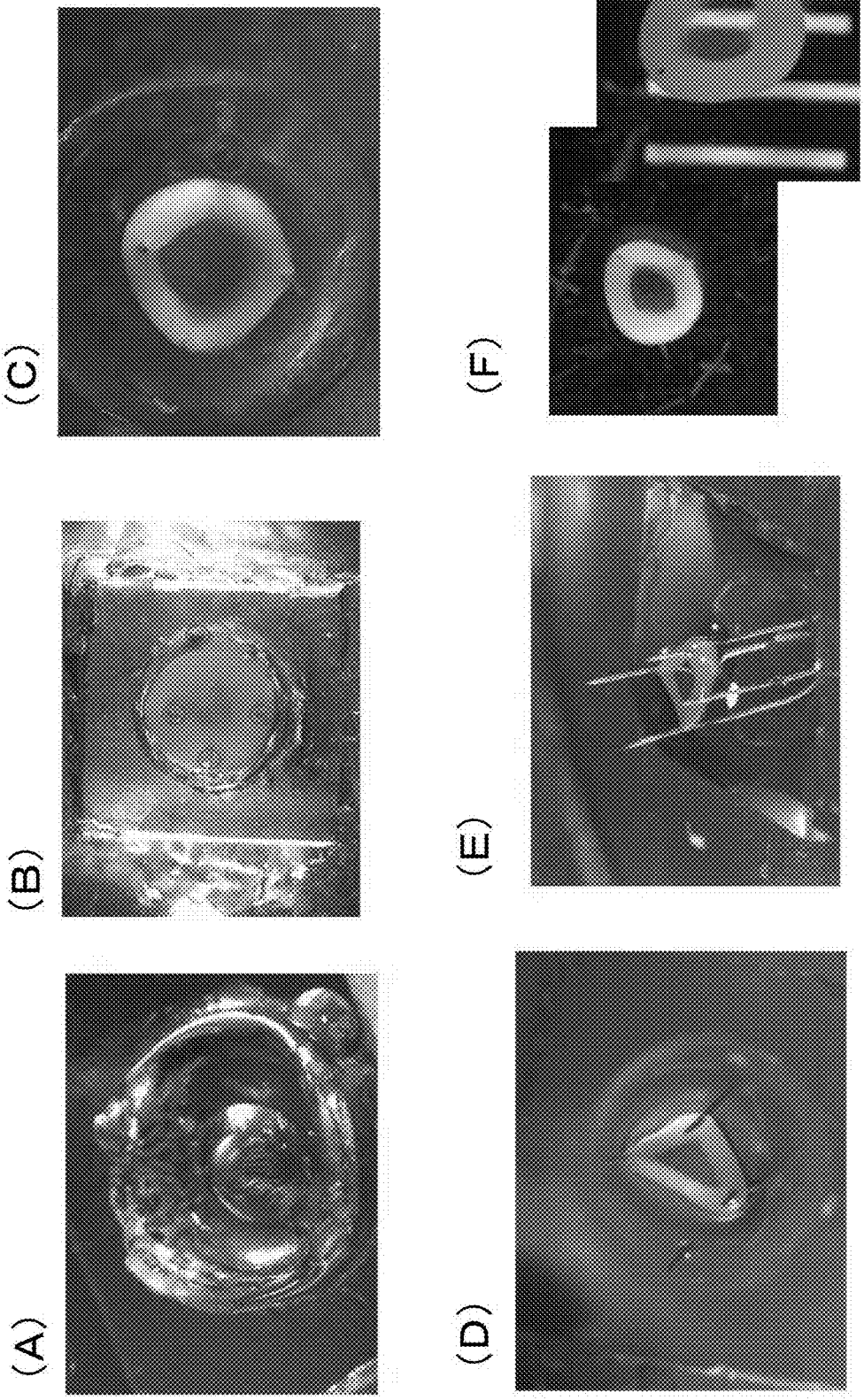
FIG. 10 is a view showing an example of producing a cell structure according to the Example.

Four needles (0.17 mm) were raised on a hat type vessel (diameter: 4 mm) made of a polydimethylsiloxane (PDMS) resin (FIG. 10A), and a cell suspension (cell count: $5 \times 10^6$ cells) was then poured into the vessel (FIG. 10B). Human fibroblasts were used as cells herein.

Three days later, it was observed that the cells aggregated and covered the needles (FIG. 10C).

By sliding the hat type vessel downwards, a ring-shaped cell structure was retained at the tip of each needle (FIGS. 10D and E). In the present invention, the cell structure in this state can be directly used in a pharmacological test, but as shown in FIG. 10F, it is also possible to remove the cell structure from the needle, and then, to subject it to a pharmacological test or to produce pathologic tissues therefrom.

DESCRIPTION OF REFERENCE NUMERALS

1: Cell culture apparatus of the present invention, 2: Pinholder-shaped member, 9: Cell testing device, 10: Cell-holding container, 11: Protruding part, 12: Side wall, 13: Recessed part, 14: Through-hole, 20: Substrate, 21 Needle-shaped body, 31: Cell suspension, 32: Cell, 33: Spheroid, 34: Cell structure, 40: Culture vessel, 90: Substrate, 91: Cell culture solution-supplying part, 92: Test substance-supplying part

The invention claimed is:

1. A cell culture apparatus having a cell-holding container and needle-shaped bodies arranged on a substrate, wherein
    the center of the bottom surface of the cell-holding container is formed in a protruding shape, the area between the center and a side wall is formed in a recessed shape, and through-holes through which the needle-shaped bodies penetrate are established on the bottom surface of the recessed shape area,
    the needle-shaped bodies are arranged in correspondence with the positions of the through-holes, and
    the needle-shaped bodies on the substrate are arranged, such that the tip-side portion of each of the needle-shaped bodies penetrates through the corresponding through-hole from the bottom surface side or upper surface side of the cell-holding container.

2. A cell culture apparatus having a cell-holding container and needle-shaped bodies arranged on a substrate, wherein
    the center of the bottom surface of the cell-holding container is formed in a protruding shape, the area between the center and a side wall is formed in a recessed shape, and
    the needle-shaped bodies on the substrate are arranged, such that the tip of each of the needle-shaped bodies is directed from the upper surface side of the cell-holding container towards the bottom surface of the cell-holding container.

3. The cell culture apparatus according to claim 1 or 2, wherein a plurality of the cell-holding containers and a plurality of the needle-shaped bodies are arranged in the form of an array.

4. The cell culture apparatus according to claim 1 or 2, wherein the cell-holding container is subjected to a cell non-adhesive coating treatment.

5. A method for producing a cell structure, comprising pouring a cell suspension into a cell-holding container of the cell culture apparatus according to claim 1 or 2, and agglutinating the cells so that the cells cover the needle-shaped bodies.

6. The method according to claim 5, wherein the cells are hepatocytes or myocardial cells.

7. A cell testing method, comprising contacting a test substance with a cell structure produced by the method according to claim 5, and testing the toxicity of the test substance to the cells or the metabolic activity of the cells in the cell structure.

8. The method according to claim 7, wherein the cells are hepatocytes or myocardial cells.

9. A cell testing device, including the cell culture apparatus according to claim 1.

10. The device according to claim 9, wherein the cells are hepatocytes or myocardial cells.

11. The cell culture apparatus according to claim 1 or 2, wherein there is only one protruding shape on the bottom surface and within said wall of said cell-holding container.

* * * * *